US006358997B1

(12) United States Patent
Clark et al.

(10) Patent No.: US 6,358,997 B1
(45) Date of Patent: Mar. 19, 2002

(54) TOCOPHEROL AND TOCOTRIENOL COMPOSITIONS

(75) Inventors: James P. Clark, Naperville; Manfred S. Dunker, Palos Park, both of IL (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 08/849,978

(22) PCT Filed: Dec. 22, 1995

(86) PCT No.: PCT/US95/16848

§ 371 Date: Aug. 22, 1997

§ 102(e) Date: Aug. 22, 1997

(87) PCT Pub. No.: WO96/19218

PCT Pub. Date: Jun. 27, 1996

(51) Int. Cl.$^7$ ........................ A61K 31/35; A61K 31/355
(52) U.S. Cl. ........................ 514/456; 514/458
(58) Field of Search ................. 514/456, 458

(56) References Cited

U.S. PATENT DOCUMENTS

| 5,157,132 A | 10/1992 | Tan et al. ............... 549/413 |
| 5,190,618 A | 3/1993 | Top et al. .................. 203/34 |
| 5,217,992 A | 6/1993 | Wright et al. ............. 514/458 |
| 5,393,776 A | 2/1995 | Pearce ....................... 514/486 |

OTHER PUBLICATIONS

Stampfer et al., "Vitamin E Consumption and The risk of Coronary Disease in Women", *The New England Journal of Medicine*, 328: 1444–9, (1993).

Rimm et al., "Vitamin E Consumption and The Risk of Coronary Disease in Men", *The New England Journal of Medicine*, 328: 1450–6 (1993).

Kardinaal et al., "Antioxidants in Adipose Tissue and Risk of Myocardial Infarction: The Euramic Study," *Lancet*, 342:1379–84 (1993).

Gaziano et al., "Beta Carotene Therapy for Chronic Stable Angina", *Circulation*, 82:III, Abstract No. 0796 (1990).

*Remington's Pharmaceutical Sciences*,Eighteenth Edition, pp 1008–1009.

*Handbook of Nonprescription Drugs*, Ninth Edition (1990), American Pharmaceutical Assn., pp 447–527, Ivey et al.

Medline Abstracts, issued 1991, Tan, D.T. et al., "Effect of a Palm–Oil–Vitamin E Concentrate On The Serum And Lipoprotein Lipids in Humans", abstract No. 91189080, Am. J. Clin. Nutr. vol. 53 (4 Suppl), 1027s–1030s.

Medline Abstract, AN:91189080, Tan, D.T. et al., Apr. 1991.*

Neilson Ph.D., W. (ed.), *Webster's New International Dictionary of the English Language*, $2^{nd}$ Edition, p. 1225, Springfield, MA. (1941).

Spraycar, M. (ed.), *Physician's Desk Reference Medical Dictionary*, $1^{st}$ Edition, p.823, Montvale, NJ (1995).

Tan, D., et al., "Effect of a palm–oil–vitamin–E concentrate on the serum and lipoprotein lipids in humans", The American Journal Of Clinical Nutrition, vol. 53(4), pp. 1027S–30S, (Apr. 1991).

Lewis Sr., R. (ed.), *Hawley's Condensed Chemical Dictionary*, $13^{th}$ Edition, pp.1111 & 1173, (1997).

* cited by examiner

*Primary Examiner*—Russell Travers
(74) *Attorney, Agent, or Firm*—John E. Drach; Aaron R. Ettelman

(57) ABSTRACT

Pharmaceutical compositions comprising natural tocotrienols and natural tocopherols are disclosed. Also disclosed is a method for preventing or treating the harmful effects of high serum cholesterol and/or lipid levels in a mammal, said method comprising orally administering approximately 100 mg to approximately 1000 mg of natural tocotrienols and approximately 100 mg to approximately 1000 mg of tocopherols to a mammal, including humans, in need of such prevention or treatment.

12 Claims, No Drawings

US 6,358,997 B1

TOCOPHEROL AND TOCOTRIENOL COMPOSITIONS

FIELD OF THE INVENTION

The present invention relates to pharmaceutical compositions comprising a combination of natural tocotrienols and natural tocopherols useful as a dietary supplement which exert a protective action on the cardiovascular system. This invention is also directed to a method for preventing treating hypercholesteremia and/or hyperlipidemia by the administration of natural tocotrienols and natural tocopherols.

BACKGROUND OF THE INVENTION

Vitamin E generally refers to the group of compounds (tocol and tocotrienol derivatives) which exhibit qualitatively the biological activity of alpha-tocopherol. They are fat soluble, closely related chemical compounds found in vegetable oils, such as wheat germ oil, rice oil, soy bean oil and the like. Alpha-tocopherol has the greatest biological activity per unit weight while its isomers beta, gamma, delta, epsilon, zeta and eta-tocopherols have vitamin E activity to a lesser extent. The tocopherols and their esters such as tocopherol acetate, tocopherol palmitate, tocopherol succinate and the like are normally water-insoluble.

Tocotrienols and tocopherols (Vitamin E) are therefore known compounds, U.S. Pat. No. 5,190,618 discloses a process for obtaining tocotrienols from palm oil.

There are many vitamin and multivitamin preparations which include vitamin E as a dietary supplement optionally along with other vitamins and trace elements. For a discussion of these preparations, see, Remington's Pharmaceutical Sciences, Eighteenth Edition (1990), Mack Publishing Company pp. 1008–1009 and Handbok of Nonprescription Drugs, Ninth Edition (1990), published by the American Pharmaceutical Association, pp. 447–527.

Tocotrienols have been implicated in the suppression of cholesterolgenesis and arterial thrombosis by inhibition of platelet thromboxane formation. See, for example, the disclosure in U.S. Pat. No. 5,157,132 and the references disclosed therein. Tocopherols (Vitamin E), on the other hand, which comprise alpha, beta, gamma and delta tocopherols are essential for normal reproduction, normal development of muscles, normal resistance of erythrocytes to hemolysis and perhaps most importantly are believed to act as an antioxidant.

High serum levels of lipids and cholesterol in humans are generally considered risk factors in the development of many cardiovascular diseases such as coronary artery disease. Consequently, many therapeutic measures have been proposed to treat hypercholesteremia and hyperlipidemia. One such measure is disclosed in U.S. Pat. No. 5,217,992 which relates to the use of tocotrienol to treat hypercholesteremia, hyperlipidemia and thromboembolic disorders.

Another approach is described in the articles, "Vitamin E Consumption And The Risk Of Coronary Disease In Women" by Stampfer et al., The New England Journal of Medicine, 328: 1444–9 (1993), and "Vitamin E Consumption And The Risk of Coronary Heart Disease In Men" by Rimm et al., The New England Journal of Medicine, 328: 1450–6 (1993), which discloses that oxidation of low-density lipoprotein (LDL) plays a role in atherosclerosis. Thus, the oxidation of LDL increases their incorporation into the arterial intima which is an essential step in atherogenesis.

A variety of dietary and drug regimen have been developed or proposed which would block the oxidative modification of LDL. These regimen usually include the ingestion of Vitamin E alone.

Thus, in the foregoing articles, investigators have studied the effect of taking vitamin E with the risk of coronary disease and observed that the use of vitamin E supplements in middle-aged women was associated with a reduced risk of coronary heart disease. Similarly, an association between a high intake of vitamin E and a lower risk of coronary heart disease was also observed in men.

In another study reported in Lancet, 342: 1379–84 (1993), it was observed that high beta-carotene intake reduced the risk of myocardial infarction. Beta-carotene has also been suggested as useful in reducing undesirable vascular events in patients with chronic stable angina. See Gaziano et al., "Beta Carotene Therapy for Chronic Stable Angina," Circulation, 82:III, Abstract No. 0796 (1990).

However, a need still exists in the art for a method for protecting a mammal, including humans, from the harmful or adverse effects of high serum cholesterol and/or lipids.

SUMMARY OF THE INVENTION

The present inventors have surprisingly discovered a method for protecting the mammalian body against high blood levels of cholesterol and/or lipids by the ingestion of natural tocotrienols and natural tocopherols, thereby reducing the risk of the development of cardiovascular disease. The art has never appreciated nor suggested such a method for the use of those natural products.

While all natural tocotrienols may be used in the practices of the present invention, tocotrienol obtained from palm oil is preferred because of its low cost and ready availability. The naturally occurring tocotrienols are predominantly the d-isomer.

The natural tocopherols useful in the practice of the present invention include all the naturally occurring tocopherols, i.e., alpha, beta, gamma and delta as well as the corresponding esters, such as the succinate.

The present invention is directed to a method for preventing or treating the harmful effects of high serum cholesterol and/or lipid levels in a mammal, including humans.

According to the present invention, natural tocotrienols and natural tocopherols are administered preferably daily to exert a protective action on the cardiovascular system of the body against high levels of cholesterol and lipids. Preferably, the active agents are administered in an oral dosage form with each dose typically containing approximately 200 to approximately 400 mg tocotrienols and approximately 150 to approximately 500 mg tocopherols per unit dose.

DETAILED DESCRIPTION OF THE PREFERRED EMBODIMENTS OF THE INVENTION

Disease prevention through management of blood serum lipids and cholesterol is an accepted clinical approach. The present inventors have surprisingly now found a method whereby the body of a mammal, including humans is protected against high levels of cholesterol and/or lipid thereby lowering the risk of cardiovascular disease.

Natural tocotrienols and natural tocopherols are derived from vegetable oils. Soy oil is the most widely used source. Sunflower, corn, peanut, reseed and cottonseed oils may also be used. Natural tocotrienol and natural tocopherols are very different from that produced by chemical synthesis, i.e., synthetic "vitamin E." While the definition of vitamin E is not consistent, for the purposes of the present invention, vitamin E refers to both tocotrienols and tocopherols.

Synthetic vitamin E is a mixture of eight different stereoisomers, only one of which is molecularly equivalent to natural vitamin E. The other seven stereoisomers have a lower biological activity. The mammalian body prefers the natural stereoisomer.

Natural vitamin E is recognized as having 36 percent greater potency than synthetic vitamin E. Recent studies suggest that natural vitamin E is probably twice as effective as synthetic vitamin E.

Natural vitamin E also remains in the body much longer than synthetic vitamin E. The seven synthetic stereoisomers are secreted into the bile and then into the intestine for removal from the body. The natural vitamin E stereoisomer, on the other hand, is returned to the bloodstream in the form of low density lipoproteins.

Any natural tocopherol or tocotrienol, its ester or compounds convertible to either tocopherols or their esters are suitable for use in the practice of the present invention.

The prior art has failed to appreciate any benefit associated with the administration of tocotrienols and tocopherols to a mammal, including humans, to prevent the harmful effects of high serum cholesterol and lipid levels. Further, the prior art has heretofore never recognized any benefit for such a method using natural tocotrienols and natural tocopherols.

According to the present invention, the daily administration of approximately 100 mg to approximately 1000 mg of natural tocopherols and approximately 100 mg to approximately 1000 mg natural tocotrienols, exhibit a protective effect against high levels of cholesterol and lipid thereby preventing or treating the subsequent development of coronary heart disease. The dosage of naturally occurring tocotrienol is preferably in the range of approximately 150 mg to approximately 500 mg, more preferably approximately 200 mg to approximately 400 mg. The dosage of naturally occurring tocopherol administered to a mammal, including humans, in need of such prevention or treatment is preferably approximately 150 mg to approximately 500 mg per oral dose. The present inventors' method is cost effective since it avoids expense medication to lower elevated level cholesterol and/or lipid.

The oral compositions of the present invention can be made by conventional compounding procedures known in the pharmaceutical art, that is, by mixing the active substances with edible pharmaceutically acceptable non-toxic inert, solid or liquid carriers and/or excipients suitable for systemic administration and conventionally used in oral dosage forms. Additionally, edible, non-toxic pharmaceutically acceptable stabilizers usually used as stabilizers in oral dosage forms or edible, non-toxic pharmaceutically acceptable salts thereof can be included in the compositions of the present invention. All the above carriers, excipients and stabilizers are intended to include only those suitable for oral administration and all are conventional and known to the pharmaceutical compounding art.

To carry out the method of the present invention the natural tocotrienols and the natural tocopherols are formulated with an inert pharmaceutically acceptable carrier, suitable for oral administration. Typical solid dosage forms include for example soft gelatin capsules, hard gelatin capsules, tablets, powders, chewable tablets and the like. Typical liquid dosage forms include emulsions, elixirs and the like. Soft gelatin capsules are preferred in the practice of the present invention. These formulations are prepared in accordance with known techniques in the art. Thus, for example the natural tocotrienols and natural tocopherols are mixed with a fixed oil, such as peanut oil. The resulting mixture is optionally blended and dispensed in gelatin capsules. Thus, the natural tocotrienols and natural tocopherols are preferably combined in the same oral dosage form, however, two separate dosage forms, one of each tocotrienol and tocopherol can be administered in two separate dosage forms.

According to the present invention, the patient ingests the capsule preferably daily to obtain the benefit of the administration of the natural tocotrienols and natural tocopherols.

In order to illustrate the practice of the present invention, the following non-limiting example is provided. It will be appreciated that a vast number of additional compositions fall within the scope of the present invention. The Example is provided by way of illustration only and is not intended to limit the invention in any way.

EXAMPLE

Approximately 200 mg of natural tocotrienols obtained from palm oil and approximately 200 mg of natural tocopherols are mixed together with approximately 200 ml of peanut oil. The oily mixture is then dispensed in soft gelatin capsule and is ready for administration to a patient.

What is claimed is:

1. A method of preventing or treating the harmful effects of high serum cholesterol and/or lipid levels in a mammal, said method comprising orally administering a daily dosage composition comprising from approximately 100 mg to approximately 1000 mg of a natural tocotrienol and from approximately 100 mg to approximately 1000 mg of a natural tocopherol to a mammal in need of such prevention or treatment.

2. The method according to claim 1, wherein the composition comprises from approximately 150 mg to approximately 500 mg of the natural tocotrienol.

3. The method according to claim 1, wherein the composition comprises from approximately 200 mg to approximately 400 mg of the natural tocotrienol.

4. The method according to claim 1, wherein the composition comprises from approximately 150 mg to approximately 500 mg of the natural tocopherol.

5. The method according to claim 1 wherein the tocotrienol is derived from palm oil.

6. The method according to claim 1, wherein the composition further comprises a pharmaceutically acceptable carrier.

7. A daily dosage pharmaceutical composition for the prevention or treatment of the harmful effects of high serum cholesterol and/or lipid levels in a mammal, said daily dosage pharmaceutical composition comprising approximately 100 mg to approximately 1000 mg of a natural tocotrienol and approximately 100 mg to approximately 1000 mg of a natural tocopherol, wherein said daily dosage pharmaceutical composition is in oral dosage form.

8. The composition according to claim 7 wherein the amount of the tocotrienol is in the range of approximately 100 mg to approximately 500 mg.

9. The composition according to claim 8 wherein the amount of th tocotrienol is in the range of approximately 200 mg to approximately 400 mg.

10. The composition according to claim 7 wherein the amount of the tocopherol is approximately 100 mg to approximately 500 mg.

11. The composition according to claim 7 wherein the oral pharmaceutical composition is a solid dosage form.

12. The composition according to claim 11 wherein the solid dosage form is a capsule.

* * * * *